(12) United States Patent
Fleming et al.

(10) Patent No.: US 7,488,606 B2
(45) Date of Patent: *Feb. 10, 2009

(54) COLLECTION DEVICE FOR LATERAL FLOW CHROMATOGRAPHY

(75) Inventors: William H. Fleming, Hillsboro, OR (US); Timothy P. Hyatt, Dundee, OR (US); Dudley B. Thomas, Portland, OR (US)

(73) Assignee: QuantRX Biomedical Corporation, Portland, OR (US)

( * ) Notice: Subject to any disclaimer, the term of this patent is extended or adjusted under 35 U.S.C. 154(b) by 258 days.

This patent is subject to a terminal disclaimer.

(21) Appl. No.: 11/207,968

(22) Filed: Aug. 19, 2005

(65) Prior Publication Data

US 2005/0277202 A1    Dec. 15, 2005

Related U.S. Application Data

(60) Continuation of application No. 10/114,913, filed on Apr. 1, 2002, now Pat. No. 6,998,273, which is a division of application No. 09/501,339, filed on Feb. 9, 2000, now Pat. No. 6,365,417.

(51) Int. Cl.
*G01N 33/53* (2006.01)

(52) U.S. Cl. ............... 436/514; 436/518; 436/541; 436/810; 435/7.1; 435/7.94; 435/287.1; 435/287.2; 435/805; 435/810; 435/970; 422/56; 422/58; 422/61

(58) Field of Classification Search .......... 436/518, 436/541, 810; 435/7.1, 7.94, 287.1, 287.2, 435/805, 810, 970; 422/56, 58, 61
See application file for complete search history.

(56) References Cited

U.S. PATENT DOCUMENTS

| 4,313,734 A | 2/1982 | Leuvering |
| 4,446,232 A | 5/1984 | Liotta |
| 4,635,488 A | 1/1987 | Kremer |
| 4,703,017 A | 10/1987 | Campbell et al. |
| 4,806,311 A | 2/1989 | Greenquist |
| 4,817,632 A | 4/1989 | Schramm |
| 4,855,240 A | 8/1989 | Rosenstein et al. |

(Continued)

FOREIGN PATENT DOCUMENTS

WO    WO 97/06439    2/1997

(Continued)

*Primary Examiner*—Bao-Thuy L Nguyen
(74) *Attorney, Agent, or Firm*—Klarquist Sparkman, LLP.

(57) ABSTRACT

A device for collecting oral liquids includes a lateral flow chromatography strip having a collection member. The collection member is separated from the remainder of the chromatography strip by a liquid impermeable removable barrier which prevents liquid in the collection member from entering the chromatography strip. Once adequate oral liquid has been collected (as indicated by a sample sufficiency indicator), the barrier is removed to allow oral liquids to flow through the strip. The liquids interact with binding partners in the strip to provide test results, such as an indication that an analyte of interest is present in the liquid. The strip may be contained in a housing with an access opening through which the removable barrier may be manipulated, and windows through which test results may be viewed. This device avoids reflux of reagents from the strip into the mouth of a test subject during use.

20 Claims, 5 Drawing Sheets

U.S. PATENT DOCUMENTS

| | | | |
|---|---|---|---|
| 4,861,711 | A | 8/1989 | Friesen et al. |
| 4,868,108 | A | 9/1989 | Bahar et al. |
| 4,943,522 | A | 7/1990 | Eisinger et al. |
| 4,999,287 | A | 3/1991 | Allen et al. |
| 5,075,078 | A | 12/1991 | Osikowicz et al. |
| 5,119,830 | A | 6/1992 | Davis |
| 5,120,643 | A | 6/1992 | Ching et al. |
| 5,229,073 | A | 7/1993 | Luo et al. |
| 5,334,502 | A | 8/1994 | Sangha |
| 5,376,337 | A | 12/1994 | Seymour |
| 5,380,492 | A | 1/1995 | Seymour |
| 5,416,000 | A | 5/1995 | Allen et al. |
| 5,451,504 | A | 9/1995 | Fitzpatrick et al. |
| 5,479,937 | A | 1/1996 | Thieme et al. |
| 5,569,608 | A | 10/1996 | Sommer |
| 5,591,645 | A | 1/1997 | Rosenstein |
| 5,609,160 | A | 3/1997 | Bahl et al. |
| 5,712,172 | A | 1/1998 | Huang et al. |
| 5,770,460 | A | 6/1998 | Pawlak et al. |
| 5,830,154 | A | 11/1998 | Goldstein et al. |
| 5,910,122 | A | 6/1999 | D'Angelo |
| 5,978,466 | A | 11/1999 | Quattrocchi |
| 6,616,893 | B1 | 9/2003 | Pham |
| 6,616,894 | B2 | 9/2003 | Lappe et al. |
| 6,716,393 | B2 | 4/2004 | Lappe et al. |
| 6,840,911 | B2 * | 1/2005 | Sangha ............... 600/582 |
| 6,875,185 | B2 * | 4/2005 | Wong et al. ............ 600/584 |
| 7,220,597 | B2 * | 5/2007 | Zin et al. ............... 436/518 |
| 7,279,136 | B2 * | 10/2007 | Takeuchi et al. ........ 422/100 |

FOREIGN PATENT DOCUMENTS

| | | |
|---|---|---|
| WO | WO 98/23958 | 4/1998 |
| WO | WO 98/39657 | 11/1998 |
| WO | WO 99/50656 | 7/1999 |

* cited by examiner

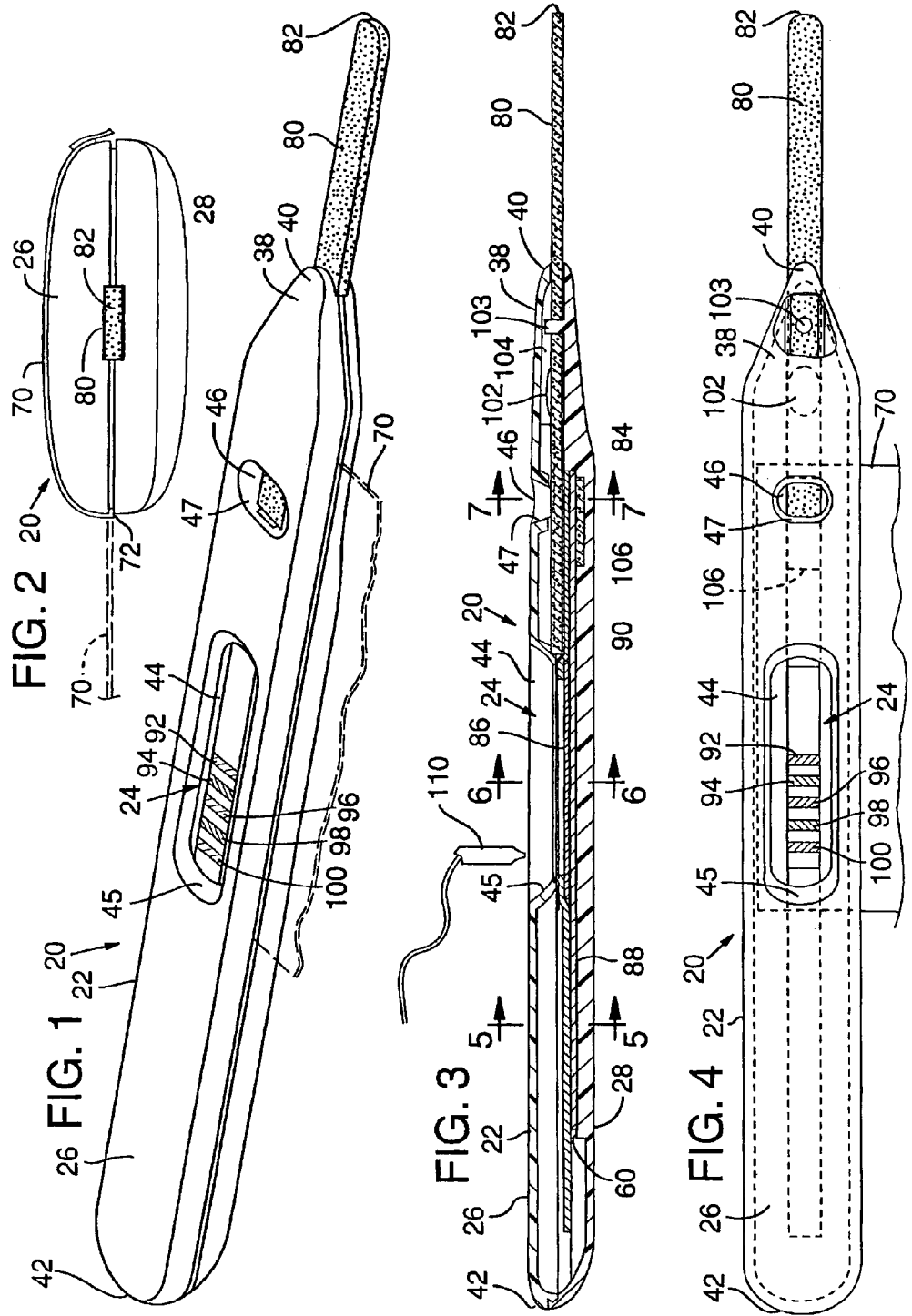

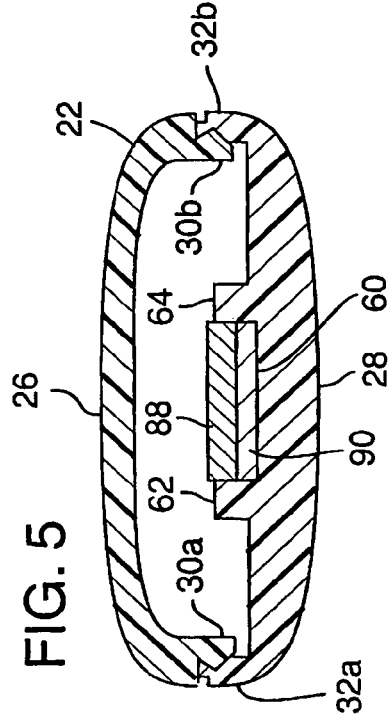

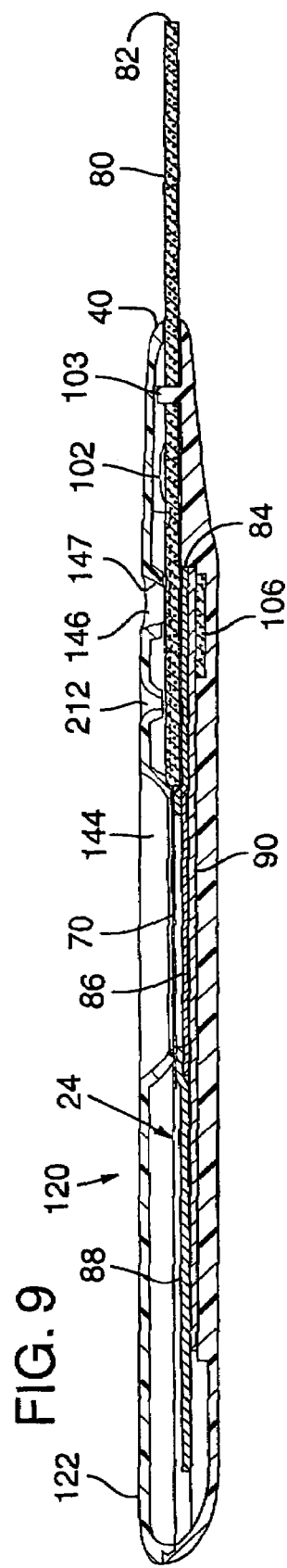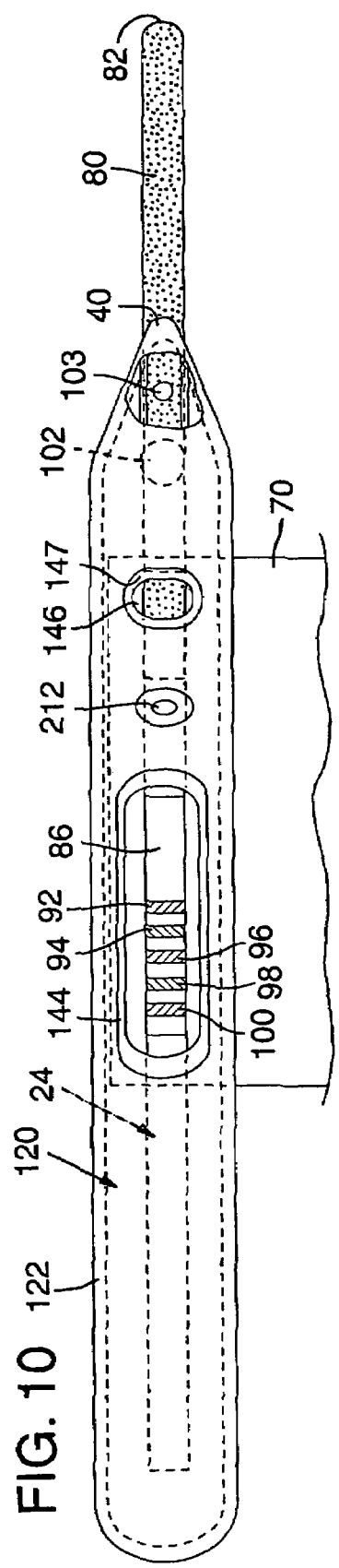

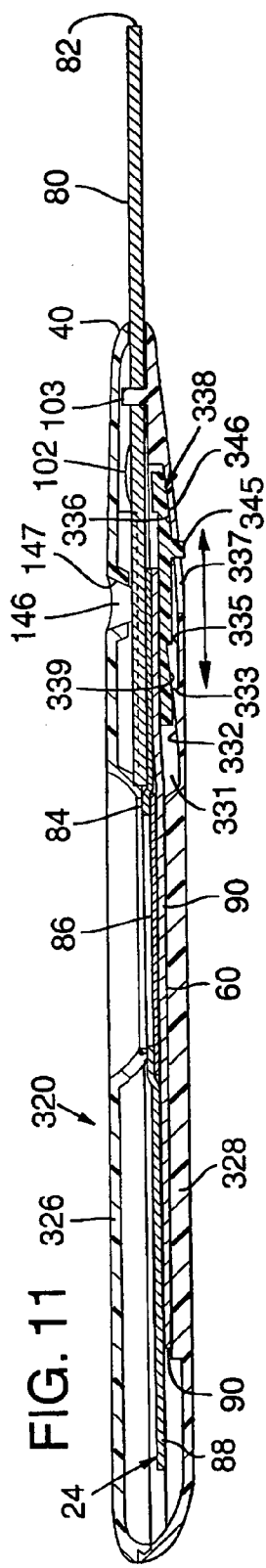
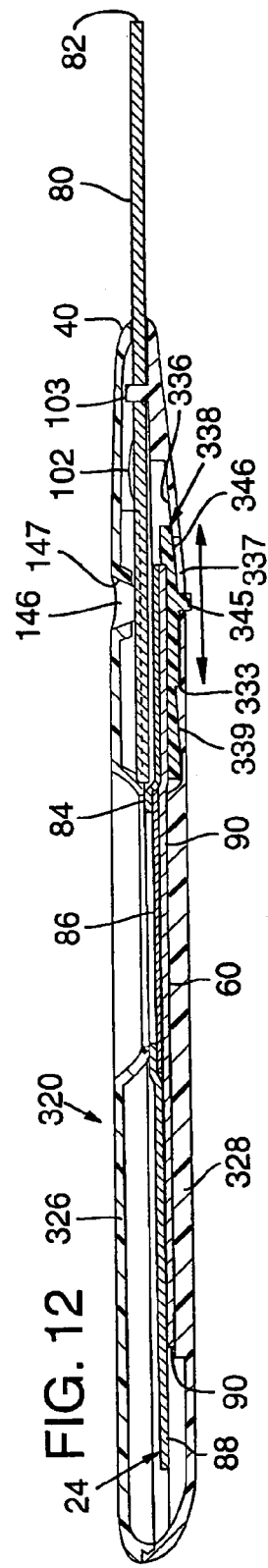
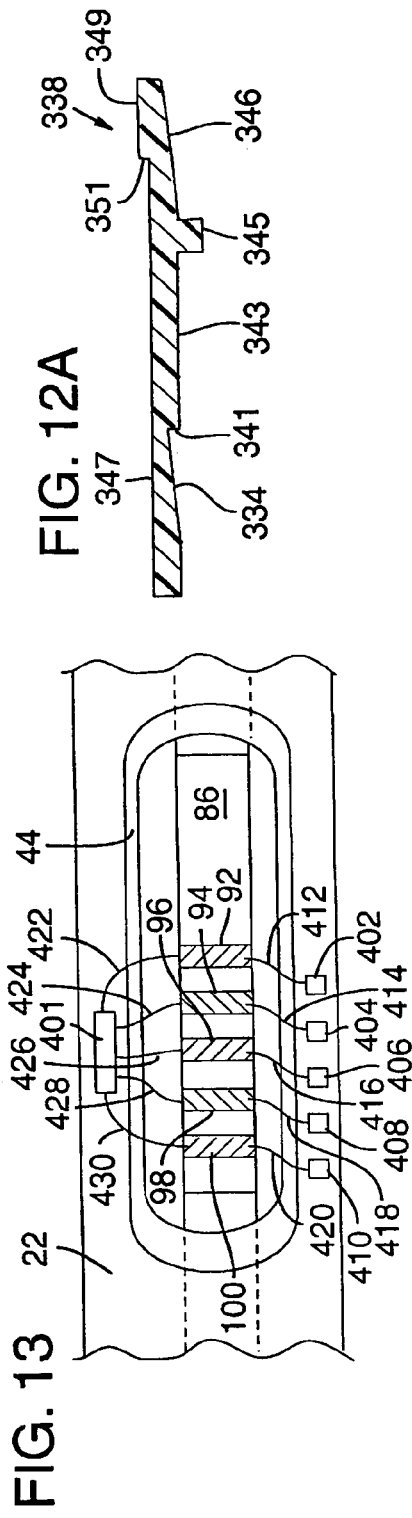

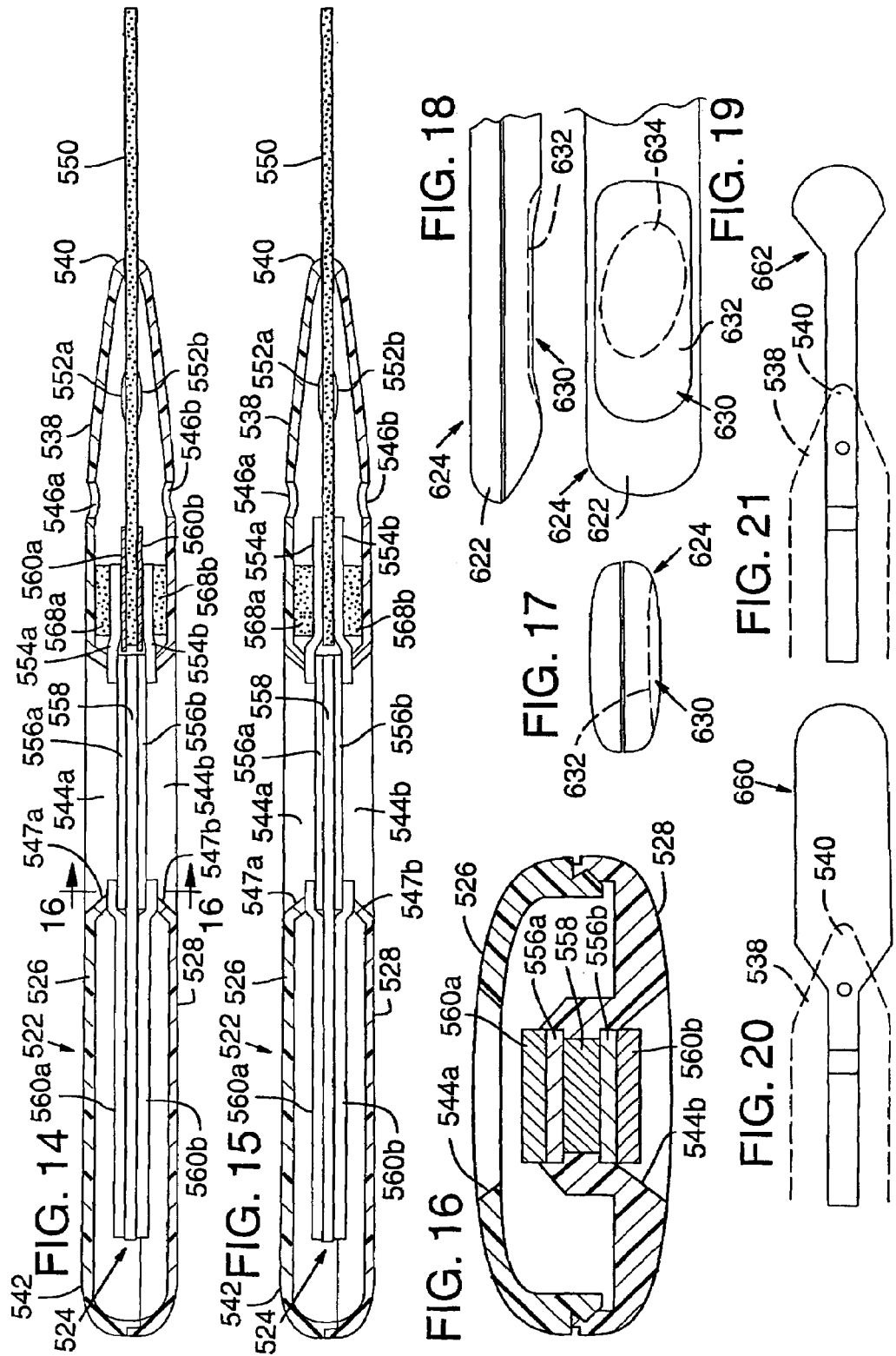

COLLECTION DEVICE FOR LATERAL FLOW CHROMATOGRAPHY

CROSS REFERENCE TO RELATED APPLICATIONS

This application is a continuation of Ser. No. 10/114,913, filed Apr. 1, 2002 now U.S. Pat. No. 6,998,273; which is a divisional of Ser. No. 09/501,339, filed Feb. 9, 2000 now U.S. Pat. No. 6,365,417. Both applications are incorporated herein in their entirety.

FIELD OF THE INVENTION

This invention relates to assays, and particularly to lateral flow assays in which a liquid analyte is applied to a sample zone of a test strip, allowed to migrate along the strip by capillary action, and detected in a capture zone.

BACKGROUND OF THE INVENTION

Assays are frequently used to detect the presence of analytes in aqueous test samples in clinical and forensic medicine, and for environmental testing, food contaminant testing, and drug use testing. There is a growing demand for such assays that are based on reactions between specifically reactive substances, and that can be conducted outside of the laboratory setting, for example at home.

There are a number of over-the-counter ("OTC") home testing and health care professional ("HCP") diagnostic devices that can be used to collect human body fluids and perform diagnostic assays. An example of such a diagnostic device is a dipstick used for midstream urine sampling, such as found in pregnancy testing, or testing of urine from a specimen placed in a receptacle. Both OTC and HCP diagnostic devices can be lateral flow devices, in which a liquid specimen is applied to a sample zone of a lateral flow chromatographic test strip. The strip is usually made of a porous carrier material (such as nitrocellulose) so that the liquid travels along the strip by capillary action to an indicator zone, which indicates a presence, absence, or quantity of the analyte. Sometimes a wick is attached to the strip to help move the liquid specimen into or along the sample zone. Numerous lateral flow analytical devices have been disclosed, and include those shown in U.S. Pat. Nos. 4,775,636; 4,703,017; 4,861,711; 4,855,240; 4,857,453; 4,943,522; 4,945,042; 4,496,654; 5,001,049; 5,075,078; 5,126,241; 5,451,504; 5,424,193; 5,712,172; and WO92/12428; WO 94/01775; and WO 97/06439, each of which is incorporated by reference.

Many lateral flow devices are one-step lateral flow assays in which a biological fluid is placed in a sample area on a bibulous strip, and allowed to migrate along the strip until the liquid comes into contact with a specific binding partner that interacts with an analyte in the liquid. Once the analyte interacts with the binding partner, a signal (such as a fluorescent dye) indicates that the interaction has occurred. Multiple discrete binding partners can be placed on the strip (for example in parallel lines) to detect multiple analytes in the liquid. The test strips can also incorporate control indicators, which provide a signal that the test has adequately been performed, even if a positive signal indicating the presence (or absence) of an analyte is not seen on the strip.

Although lateral flow devices have been widely used in clinical practice, there are still obstacles to both clinical and home use because of the difficulty obtaining some specimens (such as blood), or the reluctance of users to collect certain specimens (such as urine). Even in situations in which urine tests are widely used (such as urine analysis for drug testing), it can be awkward or distasteful to obtain the specimens for analysis. Moreover, it is sometimes difficult to positively identify a specimen as coming from a particular individual, because of the possibility that specimens have been mislabeled or exchanged after collection but before testing.

U.S. Pat. No. 5,910,122 (D'Angelo) discloses a saliva collector which encases a tip of an aspirating pipette, for subsequent analysis in a separate test. U.S. Pat. No. 5,380,492 shows another saliva collector which incorporates an indicator in the collector that changes color when sufficient saliva has been collected. U.S. Pat. No. 4,635,488 is a body fluid sampling device which has an absorbent nib that collects saliva and conducts it to an analysis element in an interior of a tube. The analysis element can be placed in the tube after saliva collection is completed. Alternatively, liquid communication between the nib and analysis element is altered by a porous, absorbent but hydrophobic disc that conducts the saliva to the analysis element after being wetted with a wetting agent.

A problem that has retarded the more widespread use of intra-oral collection devices is that regulatory agencies and test subjects have been concerned about the reverse migration or reflux of detection reagents from the device into the mouth. Such reflux could cause a test subject to experience a noxious taste, or even carry potentially harmful detection reagents into the mouth of the subject.

Many lateral flow tests are used for regulatory or legal purposes, and proper identification of the test subject is important. Prior devices have included a label on which identifying information can be written (for example, in U.S. Pat. No. 5,380,492). However, incorrect information can be intentionally or unintentionally entered on such labels.

It would be advantageous to provide a simple and convenient assay that is suitable for home use, avoids reflux of test reagents, and/or which can readily identify a person from whom the biological specimen is obtained.

SUMMARY OF THE DISCLOSURE

The present invention is a lateral flow device for analyzing analytes in a liquid, such as drug metabolites in saliva. In some of the disclosed embodiments, the lateral flow device includes a collection member which communicates with a lateral flow member that includes test result indicators which signal the presence, absence and/or quantity of analytes in a test liquid. The collection member absorbs or adsorbs a liquid (such as saliva in the mouth) to which the collection member is exposed. A removable barrier between the collection member and the lateral flow member inhibits the flow of liquid from the collection member when the removable barrier is present, but permits the liquid to flow into and through the lateral flow member when the barrier is removed. In some embodiments, a sufficiency indicator may be displayed by the collection member to indicate when a sufficient amount of saliva has been collected to remove the barrier.

In particularly disclosed examples, the barrier may be a negative barrier or a positive barrier. A positive barrier is a substantially liquid impermeable barrier, for example a substantially liquid impermeable plastic sheet. In some embodiments, the lateral flow member overlaps the collection member or abuts it in end to end contact, and the removable barrier may be a removable spacer interposed between the collection member and the lateral flow member. Alternatively, the liquid impermeable barrier may be a negative barrier, such as a gap between the collection member and the lateral flow member. Instead of removing such a barrier, the gap is closed, for example by sliding the collection member and the lateral flow member into contact with one another. In a particularly disclosed embodiment, the collection member and lateral flow member slide into an overlapping contiguous relationship.

The present device may be used for collecting oral secretions for subsequent analysis. A particularly suitable intraoral device includes a housing that holds the lateral flow member and at least a portion of the collection member, with the collection member extending outside of the housing for placement in the mouth. The removable barrier may be contained within and accessible from outside of the housing, to permit the removable barrier to be removed from the between the collection member and lateral flow member when sufficient oral secretions (such as saliva) have been collected. The housing may define one or more windows though which the test result indicators can be viewed on the lateral flow member. It may be advantageous to close the windows, with clear or magnifying materials such as glass or plastic, to help isolate the interior of the housing from the oral environment.

The housing may also include slots through which a portion of the barrier extends to an exterior of the housing. An interior portion of the barrier is interposed between the collection member and the lateral flow member, so that the external portion of the barrier may be grasped and pulled out of the housing to permit the collection member and lateral flow member to come into contiguous liquid transferring contact. Alternatively, when the barrier is a negative (e.g. gap) barrier, a sliding member may move either or both of the collection member and lateral flow member into overlapping or other contiguous contact.

When the housing is intended for insertion into a body orifice (such as the mouth), it is particularly advantageous for an anterior portion of the housing to taper toward the collection member to be more comfortably retained in the orifice. Hence when the collection member extends anteriorly out of the housing, the housing tapers in that same direction to facilitate insertion of the device into the liquid collection orifice (such as the mouth). In some embodiments, the housing also has substantially flat top and bottom surfaces, and a low profile, to fit comfortably between the dentition of a test subject.

In other embodiments, multiple lateral flow members can be used instead of a single such member. For example, two lateral flow members may be opposed back to back, in communication with a single oral collection member. A removable substantially liquid impermeable positive or negative barrier may be present between the collection member and both of the lateral flow members. Removal of the barriers allows test liquid to flow from the collection member into both of the lateral flow devices. When the lateral flow members are opposed back to back, the test results of both strips can easily be read in situ (without removal from any housing) by viewing opposite faces of the housing. However, more than two lateral flow members can be arranged in a variety of configurations, for example in a triangular or quadrilateral array.

A physical identifier region may be present on the device to interact with and identify the user. The physical identifier region may be a segregated fingerprint receiving region, such as a relatively smooth, segregated area on the housing at a position that a digit (such as a thumb) of a test subject would grasp the housing to insert it in the mouth.

In a more particular embodiment, the device includes an elongated housing having dimensions that allow the housing to be placed in a mouth of a subject. A lateral flow chromatography member is contained within the housing, and a collection member is positioned to contact the lateral flow chromatography member. The collection member is elongated and extends to outside of the housing for insertion and retention in the mouth of a subject, and a removable barrier is present between the collection member and the lateral flow chromatography member, to interrupt movement of liquid between the collection member and the lateral flow chromatography member when the barrier is in place. The collection member and the lateral flow chromatography member are both elongated and longitudinally overlap, and are spaced from one another by the removable barrier, which is substantially impervious to any liquid, regardless of the chemical characteristics of the liquid.

The housing defines an access opening though which the removable barrier is accessible for removal. The barrier is a liquid impervious sheet that extends between the collection member and the lateral flow chromatography member along a region of overlap between the collection member and the lateral flow chromatography member. An external portion of the barrier material extends through the access opening in the housing, to the exterior of the housing, so that the external portion can be grasped outside of the housing and pulled out of the housing to remove it. Once the barrier has been removed, the collection member and lateral flow member become contiguous. A bias member, such as a resilient pad, may bias at least one of the collection member or the lateral flow member into contact with one another, to improve contiguous contact between them after the barrier is removed. A window in the housing allows a test result indicator to be viewed without removing the lateral flow chromatography member from the housing.

To help assure that an adequate amount of liquid has been collected by the device before the barrier is removed, a soluble sample adequacy indicator (such as a dye) may be present on the lateral flow member. The indicator is solubilized by the collected liquid, and migrates along the collection member with liquid collected by the collection member. This flow moves the sufficiency indicator to a pre-selected position on the collection member, so that the sufficiency indicator can be viewed through a window in the housing once the pre-selected amount of liquid has been collected by the collection member. The housing may also include a liquid port through which substances can be introduced through the housing on to the lateral flow member and/or the collection member.

Any of the embodiments of the device may also include a wicking member in contact with the lateral flow chromatography member. The wicking member may be positioned to draw liquid from the collection member through the lateral flow member. For example, the wicking member may be a highly absorbent material contiguous with the lateral flow member, at a proximal and/or distal region of the liquid flow path from the mouth through the lateral flow member.

Particular embodiments of the lateral flow member include one or more analyte indicator agents that interact with an analyte in the liquid to provide a test result (such as a color change in an indicator line). Many different indicator agents may be used, such as a capture agent which captures an analyte. The capture agents may be a binding partner, such as an antibody, for example a monoclonal or polyclonal antibody. The indicator agents may be arranged in a series of indicator lines which detect different analytes. The indicator agent may provide an optical, electrical, or magnetic signal to indicate a presence of an analyte in the liquid.

The disclosed device therefore provides a two-step lateral flow device, in which the first step is collection of liquid into the collection member, and the second step is elimination of the barrier. The device can be used in a method of performing an analysis on a body fluid, by placing the collection member of the device in contact with a body fluid, allowing the collection member to collect the body fluid, and removing the barrier from between the collection member and the lateral flow member. In particular applications, the method is designed to collect oral secretions, such as saliva, by placing the device in the mouth of a test subject. In those embodiments in which a liquid sufficiency indicator is included, the barrier is not removed until the sufficiency indicator provides a signal that adequate liquid has been collected to perform the test. Once the liquid flows into the lateral flow member, a signal from the indicator(s) allows the presence, absence, and/or quantity of the analyte to be detected. In particular embodiments of the method, the test subject grasps the housing with a digit (such as the thumb) on a fingerprint receiving region of the housing, for subsequent positive identification of the test subject.

The disclosed embodiments also include a kit for detection of an analyte in a liquid, such as an oral liquid. The kit includes the collection device, and instructions for placing the device in a liquid collection cavity (such as the mouth), waiting until the collection member collects oral liquid, then removing the removable barrier.

The foregoing summary will be better understood by reference to the drawings, and the following detailed description.

BRIEF DESCRIPTION OF THE FIGURES

FIG. 1 is a top perspective view of the collection device, an external portion of the removable barrier being depicted in phantom.

FIG. 2 is an end view of an anterior tip of the device shown in FIG. 1, showing the removable barrier wrapped over a top surface of the housing to cover windows in the housing.

FIG. 3 is a longitudinal cross-sectional side view of the collection device shown in FIG. 1.

FIG. 4 is a top view of the collection device shown in FIG. 1.

FIG. 5 is a cross-section of the collection device taken along section line 5-5 of FIG. 3.

FIG. 6 is a cross-section of the collection device taken along section line 6-6 of FIG. 3.

FIG. 7 is a cross-section of the collection device taken along section line 7-7 of FIG. 3.

FIG. 8 is an isolated view of the collection and lateral flow components of the collection device of FIGS. 1-7, the components being shown separate from the housing.

FIG. 9 is a cross-sectional side view of another embodiment of the collection device, in which a liquid port is provided through the housing to introduce reagents on to the lateral flow strip.

FIG. 10 is a top view of the collection device shown in FIG. 9.

FIG. 11 is a cross-sectional side view of another embodiment of the collection device, in which a reciprocating member can slide to move the collection member and lateral flow strip into and out of contiguous, flow transferring relationship inside the housing. The reciprocating member is shown in an extended position which maintains the contiguous relationship.

FIG. 12 is a view similar to FIG. 1, showing the reciprocating member in a retracted position, in which the collection member and lateral flow strip are separated by a gap.

FIG. 13 is an enlarged top view of an embodiment of the device in which electrical contacts on the housing provide detection of indicator agents that change conductivity when interacting with an analyte.

FIG. 14 is a cross-sectional view of another embodiment of the device, in which two lateral flow strips are opposed back to back, and a removable barrier is provided between the collection member and each of the lateral flow strips.

FIG. 15 is a cross-sectional view of the device of FIG. 14, after both of the removable barriers have been removed.

FIG. 16 is a cross-sectional view taken along lines 16-16 in FIG. 14.

FIG. 17 is a posterior end view of the device, illustrating in phantom depiction the recessed fingerprint receiving area of the housing.

FIG. 18 is a fragmentary side view of the posterior end of the device shown in FIG. 17.

FIG. 19 is a bottom view of the device shown in FIG. 18.

FIGS. 20 and 21 are top views of alternative embodiments of the collection member.

DETAILED DESCRIPTION OF SEVERAL DISCLOSED EMBODIMENTS

Although many different embodiments of the invention are possible, several particular examples are disclosed in this detailed description. These examples (like the foregoing summary of the embodiments) are meant to facilitate understanding of the claimed invention, and are not intended to limit the claims to particularly disclosed or summarized embodiments.

Definitions

The following definitions and methods are provided to better define the present invention and to guide those of ordinary skill in the art in the practice of the present invention.

Analyte: a compound (e.g. drug, hormone, antigen, antibody, hapten, lectin, apoprotein, cofactor) to be measured. Examples of analytes are a drug, hormone, antigen, antibody, hapten, lectin, apoprotein, or cofactor. More specific examples are drug metabolites, for example cotinine as a marker of nicotine use, or a hormone such as human chorionic gonadotropin (HCG) as a marker of pregnancy.

Antibody: an immunoglobulin having an area on its surface or in a cavity that specifically binds to and is thereby defined as complementary with a particular spatial and polar organization of another molecule, such as a protein. The antibody may be polyclonal or monoclonal. Antibodies may include a complete immunoglobulin or fragments thereof, which immunoglobulins include different classes and isotypes, such as IgA, (IgA1 and IgA2), IgD, IgE, IgM and IgG (IgG1, IgG2, IgG3 and IgG4) etc. Fragments thereof may include Fab, Fv and F(ab')$_2$, Fab' and the like. Antibodies include chimeric antibodies made by recombinant methods.

Antigen: Any compound capable of binding with an antibody, or against which antibodies can be raised.

Binding partner: Any molecule or composition capable of recognizing and binding to a specific structural aspect of another molecule or composition. Examples of such binding partners and corresponding molecule or composition include antigen/antibody, hapten/antibody, lectin/carbohydrate, apoprotein/cofactor and biotin/streptavidin.

Comprising: Including at least.

Label: Any molecule or composition bound to an analyte, analyte, analog or binding partner that produces a signal, for example a signal detectable by visual, spectroscopic, photochemical, biochemical, immunochemical, electrical, optical or chemical means. Examples of labels include enzymes (such as horseradish peroxidase or alkaline phosphatase); radiolabels (e.g. tritiated hydrogen, or radioactive iodine, carbon or phosphorus); colloidal gold particles; colored latex particles (U.S. Pat. Nos. 4,275,149; 4,313,734; 4,373,932; 4,954,452); magnetic beads (such as DYNABEADS); and fluorescent dyes (e.g. fluorescein and rhodamine).

Lateral Flow Device: Devices that include bibulous or non-bibulous matrices capable of transporting analytes and reagents to a pre-selected site. Many such devices are known, in which the strips are made of nitrocellulose, paper, cellulose, and other bibulous materials. Non-bibulous materials can be used, and rendered bibulous by applying a surfactant to the material.

Lateral flow chromatography strip: A test strip used in lateral flow chromatography, in which a test sample suspected of containing an analyte flows (for example by capillary action) through the strip (which is frequently made of materials such as paper or nitrocellulose). The test fluid and any suspended analyte can flow along the strip to a detection zone in which the analyte (if present) interacts with a detection agent to indicate a presence, absence and/or quantity of the analyte.

Liquid impermeable: Having a physical structure that substantially prevents passage of any liquid through. For example, the liquid will not pass through even if the chemical characteristics of a barrier are changed (for example, even if a hydrophobic barrier is changed to a hydrophilic barrier by chemical treatment). Liquid impermeable barriers are often characterized by a structure that is not porous, or has pores that are too small to substantially allow any significant amounts of liquid to flow through them.

Positive/direct reporting: refers to an increase in the reporting or detection signal with increasing analyte concentration.

Specific binding agent: An agent that binds substantially only to a defined target. The determination that a particular agent binds substantially only to a protein may readily be made by using or adapting routine procedures. One suitable in vitro assay makes use of the Western blotting procedure (described in many standard texts, including *Antibodies: A Laboratory Manual* by Harlow and Lane).

As used in this specification, the singular includes the plural, unless the context clearly indicates otherwise. Hence "a" and "the" include the plural, unless otherwise indicated.

Embodiment of FIGS. 1-8

Housing with Removable Barrier

FIGS. 1-8 illustrate a first embodiment of a two-step lateral flow chromatography device 20 having a housing 22, which contains a lateral flow chromatography strip 24. Housing 22 is an elongated plastic casing, made of a thermoplastic resin such as polypropylene and which has a top portion with a substantially flat or slightly arcuate top surface 26 and bottom portion with a substantially flat or slightly arcuate bottom surface 28. The top and bottom portions of the housing snap together at complementary elongated ribs 30a, 32a and 30b, 32b (FIGS. 5-7) that extend longitudinally along the sides of the housing. The disclosed embodiment of the housing has a low profile, with a height of only about 0.2 to 0.5 inches, ideally 0.375 inches so that it fits comfortably between the dentition of a test subject when the device 20 is placed in the mouth. The substantially flat or only slightly curved top and bottom surfaces 26, 28 also provide a more comfortable profile that fits between the upper and lower teeth of a person in whose mouth the device is placed. The shape and dimensions of the housing also allow device 20 to be easily grasped and held by a human hand.

Housing 22 has an anterior tip 38 (FIGS. 1-4) that tapers to a narrow nose 40, and a rounded posterior end 42. In the embodiment of FIGS. 1-7, the housing defines an elongated test result view window 44 which extends longitudinally along housing 22 at a mid-portion thereof, and a smaller somewhat ovoid indicator window 46 between window 44 and nose 40. A peripheral lip 45 of window 44 extends downwardly into the housing, as does a peripheral lip 47 of window 46, but the peripheral edge 47 in shorter than peripheral lip 45. Transparent glass or plastic covers 48, 50 (FIGS. 6 and 7) are disposed in windows 44, 46, and provide a barrier against passage of liquid into housing 22. The covers 48, 50 may be non-magnifying, or one or both of them may have positive dipotric power to magnify any indicia on the strip 24 exposed through windows 44 and/or 46. Cover 50 (FIG. 7) is thick, and extends deep into window 46 to form a positioning member that includes two longitudinally extending ridges 52, 54 that cooperatively define a recess 56 therebetween.

A longitudinal recessed channel 60 (FIGS. 5 and 6) extends along the interior of housing bottom 28, and is deepest at an anterior portion of housing 22 (FIGS. 3 and 7), but of a lesser depth toward the middle and posterior portion of the housing (FIGS. 5 and 6). Channel 60 is formed by a pair of lower ribs 62, 64 that are higher at the middle section of housing 22 (FIG. 6) than at the posterior section (FIG. 5). Peripheral lip 45 of window 44 extends downwardly from the interior of the housing top 26, and forms a narrow slot between lower ribs 62, 64 and lip 45. A removable barrier sheet 70 extends through the narrow slot, and out of a slot 72 of corresponding length, which is formed between top and bottom sections 26, 28 of the housing. The sheet is made of a liquid impermeable material, such as Mylar, Polypropylene, or Vinyl. As shown in FIGS. 1 and 2, the sheet is of sufficient dimensions to wrap over top 26 of housing 22, and cover windows 44, 46 (FIG. 2).

Chromatography strip 24, which is seated in housing 22, is seen in isolation in FIG. 8, which shows strip 24 to include an elongated, narrow, bibulous liquid collection member 80 with a rounded anterior tip 82 for insertion in a body orifice, such as a mouth. Collection member 80 absorbs or adsorbs liquid, which flows in a path 81 proximally from tip 82, and overlaps a proximal wick 84. The proximal wick 84 overlaps a subjacent lateral flow member 86, which is in turn overlapped by a distal wick 88. The lateral flow member 86, and the distal and proximal wicks 84, 88 are mounted on a rigid plastic support 90 (for example by lamination or adhesion) which maintains the relationship illustrated in FIG. 8.

Capture agents (such as specific binding partners, for example monoclonal antibodies) are aligned as indicator lines 92, 94, 96, 98, 100 (FIG. 4) on lateral flow member 86. Although the capture agents can be designed to perform a variety of direct and indirect assays (such as immunoassays), the illustrated embodiment incorporates different monoclonal antibodies in each indicator line. The monoclonal antibodies are attached to the substrate in a known fashion, and each recognize a different potential analyte in the liquid (such as a metabolite of a drug of abuse), and provide an indication (such as a change in color, electrical conductivity, fluorescence, or magnetic polarity) if the analyte binds to the capture agent.

In FIGS. 3 and 8, liquid impermeable sheet 70 is shown interposed between collection member 80 and proximal wick 84. Sheet 70 is sufficiently long in the disclosed embodiment to extend at least the length of the overlap between member 80 and proximal wick 84, and additionally cover lateral flow member 86 and a portion of distal wick 88.

FIGS. 1-7 show chromatography strip 24 seated in housing 22, with collection member 80 extending from nose 40, which closely engages the collection member to help exclude entry of liquid into the housing other than through collection member 80. A positioning pin 103 (FIGS. 3-4) extends through collection member 80 to help fix it in position, and resist longitudinal shifting of member 80. A liquid soluble indicator dye 102 (FIG. 3), such as FD&C blue or light blue dye, applied as a liquid then dried, is provided on the top surface of collection member 80, at a position between nose 40 and view window 44. There is a clearance 104 (FIG. 3) between the top surface of collection member 80 and housing 22 (including peripheral lip 47) to permit free flow of liquid (and any solubilized indicator dye 102), without interference from the housing. This clearance also allows the collection member to expand as liquid moves into and through it, and thereby avoids physical restriction of the collection member.

When strip 24 is seated in housing 22, support 90 is seated on the bottom of housing 22, within the channel 60 (FIGS. 5 and 6) formed between ribs 62, 64. Beneath a region of overlap between collection member 90 and anterior wick 84 is a resilient foam pad 106 (FIGS. 3 and 7) recessed into the bottom of housing 22, to bias wick 84 upwardly against collection member 80. Ridges 52, 54 of cover 50 (FIG. 7) abut against lateral edges of the top surface of collection member 80, to help hold the collection member in position while minimally interfering with the flow of liquid along the collection member.

In operation, device 20 (with barrier sheet 70 wrapped around the housing as in FIG. 2) is introduced into the mouth by inserting anterior tip 38 between the teeth of a test subject (not shown), and placing collection member 80 between the tongue and palate for retention there when the teeth bite down on top and bottom 26, 28 of housing 22. Alternatively, the tip can be placed in other positions, such as sublingually or adjacent the buccal mucosa, and saliva or other oral secretions are collected. With device 20 in situ in the mouth, housing 22 extends from the mouth so that indicator window 46 is visible externally. As saliva moves into and through collection member 80, indicator dye 102 is solubilized and moved along collection member until it reaches indicator window 46. The collection device has been pre-calibrated such that arrival of dye 102 in window 46 signals that sufficient liquid has been collected to perform the analytical tests for which device 20 is designed.

Once the indicator signal is observed, device 20 may be removed from the mouth, and the external portion of sheet 70 peeled away from housing 22 (to the position shown in phantom lines in FIGS. 1 and 2). The external portion of the sheet is then grasped and pulled to remove sheet 70 through slot 72, which allows collection member 80 and subjacent proximal wick 84 to overlap contiguously. This contiguous contact is promoted by resilient pad 106, which is pre-compressed and therefore expands when barrier 70 is removed, such that wick 84 is pushed upwardly against overlying collection member 80. This movement tightly contiguously engages wick 84 and collection member 80, to promote more efficient liquid transfer from collection member 80 to wick 84.

Liquid then moves from wick 84 into and through lateral flow member 86 by capillary action. As the liquid encounters the capture agents in indicator lines 92-100, the capture agents undergo a physical and/or chemical transformation, that can be detected visually, or by a sensor 110. This transformation can indicate the presence, absence, and/or quantity of an analyte in the liquid. Continued distal flow of liquid distally through strip 24 is encouraged by distal wick 88, which absorbs and draws liquid toward it. Wick 88 also acts as a reservoir for collecting the liquid.

Once the test has been performed, device 20 can be discarded or recycled for reuse.

Embodiment of FIGS. 9-10

Housing with Liquid Reagent Inlet Port

Another embodiment is shown in FIGS. 9-10, in which a collection device 120 holds a lateral flow chromatography strip 24 identical to that shown and described in connection with FIGS. 1-8. Since strip 24 is identical to that shown in the earlier embodiment, the same reference numerals are used to identify its component parts. Device 120 has a test view window 144 through which are viewed indicator lines 92-100, and a sufficiency indicator window 146 through which is viewed solubilized indicator dye 102 after it migrates with liquid collected by collection member 80.

This embodiment differs from FIGS. 1-7 in that housing 122 includes an additional opening in the form of a liquid entry port 212 which extends through the housing and opens over chromatography strip 24 distal to the termination of collection member 80. Port 212 is suitably positioned between windows 144 and 146, so that it will be external of the mouth when device 120 is positioned in the mouth for collection of oral fluids. The width of port 212 tapers as it extends internally in the housing, and it is suitable for introducing reagents such as conjugate, chase buffer, or solubilizing buffer to strip 24. The operation of device 120 is otherwise the same as described in connection with FIGS. 1-8.

Embodiment of FIGS. 11-12

Sliding Platform to Close Negative Barrier Gap

Another embodiment of the invention is shown in FIGS. 11-12, in which a chromatography strip 24 is shown in a different housing 320 having a top 326 and a bottom 328. Bottom support 90 of strip 24 rests in a channel in bottom 328, with collection member 80 overlapping proximal wick 84, which in turn overlaps lateral flow member 86, which is in turn overlapped by distal wick 88. Strip 24 is not provided with a removable barrier sheet, but instead has a "negative" barrier provided by a gap between collection member 80 and its subjacent proximal wick 84 (FIG. 12). An anterior portion of the channel includes a deeper region 331 with a bottom surface 332 that is upwardly sloped in an anterior direction to a transverse ridge 333 having a flat anterior face. The anterior channel is subsequently recessed to a flat surface 335, which gradually becomes an upwardly inclined surface 336 toward nose 40 of device 20. A slot 337 is provided through flat surface 335 of bottom 328.

A sliding ramp 338 (shown in isolation in FIG. 12A) is disposed in the anterior portion of the channel, and presents a bottom surface that is complementary to the shape of the anterior channel surface. Ramp 338 has a sloped posterior bottom surface 339 (complementary to housing surface 332) that rises to a vertical stop surface 341 (complementary to ridge 333) which connects surface 339 with a non-sloping surface 343 (complementary to surface 335 of housing 320). A tab 345 extends downwardly from ramp 338, and a bottom surface 346 of the ramp anterior to tab 345 slopes slightly upwardly (complementary to housing surface 336). A top ledge 347 of ramp 338 is substantially flat, but ledge 347 has a raised front 349 that presents an upwardly extending stop surface 351.

In use, ramp 338 is placed in the channel, with tab 345 protruding through the bottom slot to the exterior of the housing. In this position, ramp 338 can be manipulated (by pushing tab 345 forward and backward) between a retracted position (FIG. 12) and an extended position (FIG. 13). In the retracted position, top ramp ledge 347 is slightly lower than channel surface 60 on which strip 24 is supported, while in the extended position, ledge 347 is at the same level or higher than channel surface 60. With ramp 338 in the retracted position (FIG. 12), the anterior end of chromatography strip 24 rests on ledge 347, with the leading edge of strip 24 abutting stop surface 351. In this position, the bottom surface of ramp 338 conforms to the complementary shape of the bottom surface of the region 331 of housing bottom 328.

The front of strip 24 (supported by ledge 347) is slightly lower than the main body of the strip supported by channel surface 60, and there is a gap 360 of about 1.00 to 1.50 mm between distal collection member 80 and the top surface of proximal wick 84. However, when ramp 338 is pushed to the extended position (FIG. 11) by engaging tab 345 and sliding it toward nose 40, inclined surfaces 339, 346 of ramp 338 slide up inclined surfaces 332, 336 of the housing, which raises ramp 338 up from surface 335. As the height of ramp 338 is raised, the front portion of strip 24 moves toward overlying collection member 80, to close gap 360 and bring strip 24 into close contiguous contact with the collection member.

With ramp 338 in the retracted position of FIG. 12, collection member 80 is placed in the mouth of a test subject and allowed to collect oral secretions until indicator dye 102 is solubilized and moves to the indicator window. After the indicator dye appears in the window, tab 345 is moved toward tip 40, to raise strip 24 and close gap 360, which allows saliva or other liquid in collection member 80 to move into wick 84 and through lateral flow member 86 to perform the test. Ramp 338 can be moved while device 320 is still retained in the mouth of the test subject, or following removal of the device from the mouth. The test results are obtained by detecting a change in the indicator lines of the lateral flow member.

Embodiment of FIG. 13

Detecting Changes in Electrical Conductance in Indicator Lines

FIG. 13 shows an enlarged view of the central portion of housing 22 of FIGS. 1-7, in which window 44 exposes indicator lines 92-100, in which capture agents are immobilized. As previously noted, the capture agents can be designed to changed electrical conductance to indicate a result. For example, electrical conductance can change when an analyte is present in the liquid. Should the conjugate solution contain colloidal gold or similar conductive material, the conductivity across the lateral flow device will decrease as more binding occurs at that site.

Housing 22 is provided with a first electrical contact 401 along one edge of window 44, and a series of adjacent metallic electrical contacts 402, 404, 406, 408 and 410 through housing 22 along an opposing edge of window 44. Each of the contacts 402-410 corresponds to a respective one of indicator lines 92-100, and is connected to a transverse edge of its respective indicator line by a conductor, such as an electrically conductive wire 412, 414, 416, 418 or 420. An opposing transverse edge of each indicator line is connected to a conductor, such as wires 422, 424, 426, 428 or 430 which all lead to conductor 401. An electrical circuit (not shown) can be used to establish an electrical potential across contact 401 to contacts 402-410, so that an electrical current can flow between contact 401 and one or more of contacts 402-410 when one or more of indicator lines 92-100 becomes electrically conductive.

When the indicator line is intended to provide a signal about the presence, absence, and/or quantity of an analyte in the liquid, the electrical conductivity of the indicator line changes. The change in electrical conductivity can be detected by a flow of electrical current through a respective contact 402-410. For example, if indicator lines 94 and 98 capture an analyte, the electrical conductivity of the line changes, such that an electrical current flows from contact 401, through wires 424 and 428, indicator lines 94, 98, wires 414, 418, and contacts 404, 408. The flow of electrical current through contacts 404, 408 can be detected by a current flow meter, to measure a positive reaction. The level of current detected can also be used as an indicator of the positivity of the reaction.

Embodiment of FIGS. 14-16

Dual Sided Test Strip

Yet another embodiment of the invention is shown in FIGS. 14-16, which discloses a two-sided lateral flow chromatography strip 524 that can be used with or without a housing 522. The optional housing 522 (which is similar to that illustrated in FIGS. 1-7) has complementary, mirror image top and bottom portions, which present parallel top surface 526 and bottom surface 528, and further includes an anterior tip 538 which tapers to a narrow nose 540, and a posterior end 542. A test view window 544a extends through top surface 526, while a corresponding opposing test view window 544b extends through bottom surface 528. An indicator window 546a is provided through top surface 526, while a corresponding opposing indicator window 546b is provided in bottom surface 528. A peripheral lip 547a, 547b extends inwardly from windows 546a, 546b to help center strip 524 in housing 522.

Strip 524 includes an elongated absorbent or adsorbent collector strip 550 having parallel planar top and bottom faces, with an indicator dye 552a, 552b localized on the opposing faces of the strip. A distal end of strip 524 is sandwiched between a pair of anterior wicking strips 554a, 554b. The distance between strips 554a, 554b widens in a distal direction, so that their inner faces receive between them a pair of lateral flow members 556a, 556b which are mounted on and extend partially the length of a rigid plastic support 558. Lateral flow members 556a, 556b are laminated or otherwise adhered to opposing faces of support 558, and extend along support 558 at least the distance of windows 544a, 544b. The distal ends of lateral flow members 556a, 556b are sandwiched between and adhered to the ends of a pair of posterior wicking strips 560a, 560b, which are laminated or otherwise adhered distally to the top and bottom surfaces of support 558, and sandwich the lateral flow members 556a, 556b therebetween.

The lateral flow members 556a, 556b each include a plurality of indicator lines on their outer faces (not shown, but similar to those in FIG. 4) that may be viewed through their respective windows 544a, 544b. Each of the lines may contain different capture agents, and the back to back lateral flow members can double the number of tests that may be performed at a single time. Alternatively, the test(s) performed by one lateral flow member can be the same as those performed on the other lateral flow member, such that the results on one act as a confirmation of the results on the other. Another alternative is that the test results displayed on one member can detect analytes of interest, while the other member will serve as a control test for analytes that would be expected to be present (such as salivary enzymes that are usually present in oral secretions). Although the illustrated embodiment shows the lateral flow apparatus laminated to opposing faces of a rigid support 558, the strips could be fashioned using many alternative approaches, for example placing capture agents on opposing faces of a sufficiently thick lateral flow member. Similarly, although the wicks are shown overlapping the lateral flow member, they can be coplanar with it.

In other embodiments (not illustrated), more than two lateral flow members could be used, for example four such members, with a surface of each of the different lateral flow members facing through a different test window of a multi-sided or cylindrical housing 522.

In FIG. 14, a liquid impermeable sheet 560a is positioned between collection strip 550 and top anterior wick 554a, while a similar liquid impermeable sheet 560b is positioned between collection strip 550 and bottom anterior wick 554b. Sheets 560a, 560b extend completely along any areas of overlap between wicks 554a, 554b and collection strip 550, to prevent direct contact between them. The liquid impermeable sheets are removable from the position shown in FIG. 14. Portions of the sheets may extend to outside of housing 522, so that the exterior portions can be grasped and pulled to remove sheets 560a, 560b from their blocking positions. Once the sheets are removed, as shown in FIG. 15, collection strip 550 contacts wicks 554a, 554b, to establish a flow path from collection strip 550, through wicks 554a, 554b, respectively into lateral flow members 556a, 556b. Each of the top and bottom posterior wicks 560a, 560b acts as a reservoir for liquid that flows through respectively through lateral flow members 556a, 556b, and also encourage continued distal flow.

In an alternative embodiment (not illustrated), collection strip 550 may be coplanar with but spaced from a wicking element and lateral flow member. Instead of separate barrier sheets, an absorbent member can be placed between the collection strip and wicking elements to establish a flow path from the collection member to the lateral flow member.

When used with housing 522, strip 524 is placed in housing 522 with collector strip 550 extending proximally from, and retained in position by, nose 540 of housing 522. A pair of resilient, compressed, top and bottom pads 568a, 568b are respectively Provided between anterior wicks 554a, 554b and the top 526 and bottom 528 of housing 522, to help secure strip 524 in a neutral position between the top and bottom of the housing. Pads 568a, 568b may be made of a liquid impermeable material, or of an absorbent material that expands when moistened. A central portion of strip 524 can also be held in a neutral position (half way between the top and bottom of the housing) by peripheral lips 547a, 547b of windows 544a, 544b.

In use, collection strip 550 can be placed in the mouth where it collects liquid at least until indicator dyes 552a, 552b are solubilized by the collected liquid and migrate to a position at which they can be viewed through indicator windows 546a and 546b. Barrier sheets 560a, 560b are then removed from housing 522, so that liquid flow is permitted to occur in a distal flow direction toward and through lateral flow members 556a, 556b. The indicator agents in the indicator lines on the lateral flow members then indicate the presence, absence, and/or quantity of a number of different analytes in the liquid.

Embodiment of FIGS. 17-19

Test Subject Identifier

Certain embodiments of the device may also be provided with an identifier, such as an identifier that interacts physically with a user to uniquely identify the test subject. An example of such an identifier is shown in FIGS. 17-19, which illustrates a posterior end 622 of a housing 624 (similar to posterior end 42 of housing 22 in FIGS. 1-4). FIGS. 17-19 illustrate that a bottom surface of the posterior end of housing 624 is slightly recessed inwardly, to form a segregated identification region with an arcuate fingerprint receiving smooth surface 632. Although this segregated region is shown as recessed, other types of segregated surfaces can be used, such as an area of different coloration or texture on housing 624. The surface 632 is positioned where a user of the device would naturally place a thumb when grasping housing 624. This placement of the thumb would leave a fingerprint, which is shown schematically by oval 634 in FIG. 19.

The fingerprint could be used to positively identify the person from whom the specimen was taken. This may be important, for example, if the test is performed to detect drugs of abuse in an employee or prison inmate, or indicators of disease in a person undergoing an insurance physical. The fingerprint identification is particularly useful in legal or other administrative proceedings, in which the identity of the test subject may be at issue.

Other physical identifiers that substantially uniquely identify the test subject could also be used. For example a dried blood or saliva drop on an absorbent pad, would provide a sample for DNA identification.

Embodiments of FIGS. 20 and 21

Alternative Collector Configurations

Although the collector member was shown as an elongated strip of constant width and thickness in earlier illustrated embodiments, the collector member (like many other aspects of the invention) can take quite different forms. Two variations in the shape of the collector member are shown in FIGS. 20-21, where the collector member is shown protruding from the tapered nose 540 of anterior tip 538 of the housing. The collector member 660 of FIG. 20 is paddle shaped, but tapers in width near tip 540 to assume a narrow width of the lateral flow strip in the housing. Alternatively, as shown in FIG. 21, a collector 662 may have an enlarged tip which tapers to the width of the remainder of the strip well before it reaches tip 540.

EXAMPLE 1

The preferred embodiment of the device is injection molded using white polypropylene plastic (as shown in FIG. 1), and has a finished overall length of $5\pm\frac{1}{32}$ inch, a width of $\frac{5}{8}\pm\frac{1}{32}$ inch, and a finished height (depth) of $\frac{3}{8}\pm\frac{1}{32}$ inch.

The device is molded in two pieces, an upper piece and a lower piece, with interlocking tabs along the long sides to hold the two pieces together in the correct relationship. The posterior ends of the device are shaped (rounded) to present an attractive appearance. All other surfaces are chamfered to eliminate all sharp edges, with a chamfer radius of about 0.015625 inch. The upper and lower piece together cooperatively define therebetween a slot for the oral collection device in the anterior tip with sufficient dimension (height and width) so as not to interfere with the sample flow from the oral collector to the proximal wick (e.g. 84 in FIG. 8).

The device includes a sufficiency indicator window (46 in FIG. 1) in the upper piece 26 of the housing, that is ³⁄₁₆±¹⁄₆₄ inch dia. and positioned with it's center 1±¹⁄₆₄ inch from the anterior tip. A test result view window 44 is ⅞±¹⁄₆₄ inch in length along the longitudinal axis and ⁷⁄₃₂±¹⁄₆₄ inch in width, and is positioned with it's center 2¹⁄₆₄±¹⁄₁₆ inch from the anterior tip.

The lower piece has a longitudinal channel molded into it to hold the test strip. The width of this channel is 5 mm+0.5 mm. This channel has positioning ribs along its length that are 1 mm, +0.0 mm, −0.5 mm in height above the base of the channel, and are 2¾ inch long and with the center point 1⅞ inch from the anterior end. The height of the channel from the bottom of the lower piece to the top of the bottom of the channel is designed to bring the proximal wick up to the upper edge of the lower piece. The lower piece also has a positioning pin (e.g. 103 in FIG. 4) molded into the anterior end, with a diameter of ¹⁄₁₆ inch and located ⅛ inch from the anterior end, and a height from the bottom of the lower piece to the top of the positioning pin of ³⁄₃₂ inch. The bottom of the anterior end of the lower piece is molded to form the support for the oral collector and the base for the positioning pin.

There is a void in the lower piece extending from the distal end of the rigid plastic support (e.g. 90 in FIG. 8) to the end of the lower piece to allow for extended capacity distal wick options.

Having illustrated and described the principles of the invention in several embodiments, it should be apparent to one skilled in the art that the invention can be modified in arrangement and detail without departing from such principles. We claim all modifications coming within the spirit and scope of the following claims.

We claim:

1. A lateral flow device for analyzing analytes in a liquid sample, comprising:
    a collection member having a collection pad for absorbing a liquid sample, wherein said collection member communicates with a lateral flow member to which the collection member is exposed;
    a lateral flow member along which liquid moves from the collection member, the lateral flow member also including an indicator agent that indicate an absence, presence and/or amount of the analyte; and
    a removable barrier located between the collection member and the lateral flow member that inhibits the flow of liquid from the collection member when the removable barrier is present but permits the liquid to flow into and through the lateral flow member when the barrier is removed.

2. The lateral flow device of claim 1, wherein the removable barrier is substantially liquid impermeable.

3. The lateral flow device of claim 1, wherein the collection member overlaps the lateral flow member, and the removable barrier is a removable spacer interposed between the collection member and the lateral flow member.

4. The lateral flow device of claim 1, further comprising a sample sufficiency indicator on the collection member that indicates when a sufficient amount of liquid has been collected by the collection member to analyze analytes in the liquid.

5. The lateral flow device of claim 1, wherein the indicator agent comprises one or more indicators on the lateral flow member that indicate the absence, presence and/or amount of the analyte in the liquid.

6. The lateral flow device of claim 1, further comprising a housing that holds the lateral flow member, and at least a portion of the collection member, and the removable barrier is accessible from outside of the housing, to allow the removable barrier to be removed to permit the liquid to flow into and through the lateral flow member when the barrier is removed.

7. A lateral flow device for analyzing analytes in a liquid sample, the device comprising:
    a collection member which collects the liquid sample for analysis;
    a lateral flow member along which liquid moves from the collection member, the lateral flow member also including an indicator agent that indicates an absence, presence and/or amount of the analyte; and
    a removable barrier between the collection member and the lateral flow member that inhibits the flow of liquid from the collection member when the removable barrier is present but permits the liquid to flow into and through the lateral flow member when the barrier is removed;
    a housing that holds the lateral flow member within the housing, wherein the housing defines an opening through which the collection member communicates with the lateral flow member that is disposed inside of the housing.

8. The lateral flow device of claim 7, wherein the lateral flow member comprises multiple lateral flow members.

9. The lateral flow device of claim 8, wherein the multiple lateral flow members comprise two lateral flow members opposed back to back.

10. The lateral flow device of claim 7, further comprising a physical identifier region on the housing that interacts with a user to identify the user.

11. The lateral flow device of claim 10, wherein the physical identifier region is a fingerprint receiving region.

12. The lateral flow device of claim 7, wherein the housing includes a segregated smooth surface fingerprint receiving region.

13. The lateral flow device of claim 7, wherein a portion of the barrier extends to an exterior of the housing through an opening in the housing.

14. The lateral flow device of claim 7, wherein the barrier is removable from outside the housing to permit the flow of the liquid from the collection member to the lateral flow member when the removable barrier is removed.

15. The lateral flow device of claim 14, wherein the housing tapers toward the collection member in the direction that the collection member extends to the exterior of the housing.

16. The lateral flow device of claim 15, wherein the housing presents substantially flat top and bottom surfaces.

17. A method of performing analysis on a liquid sample, comprising:
    placing the collection member of the device of claim 7 in contact with the liquid sample;
    allowing the collection member to collect the liquid sample; and
    removing the removable barrier from between the collection member and the lateral flow member, whereby the liquid sample moves from the collection member to the lateral flow member.

18. The method of claim 17, wherein the liquid sample is oral liquid.

19. The method of claim 17, wherein the collection member further comprises a sample sufficiency indicator on the collection member that indicates when a sufficient amount of liquid sample has been collected by the collection member to analyze analytes in the liquid sample, and the method further comprises:

allowing the collection member to collect the liquid sample until the sample sufficiency indicator indicates that a sufficient amount of liquid sample has been collected by the collection member; and removing the removable barrier from between the collection member and the lateral flow member once the sufficient amount of liquid has been collected by the collection member and detecting whether any of the indicators indicate the absence, presence and/or amount of the analyte in the liquid sample.

20. A kit for detection of an analyte in an oral liquid, the kit comprising:

the device of claim 7;

instructions for placing the device in a mouth, waiting until the collection member collects oral liquid, then removing the removable barrier.

* * * * *